(12) United States Patent
Brown et al.

(10) Patent No.: US 7,501,548 B2
(45) Date of Patent: Mar. 10, 2009

(54) OLIGOMERIZATION OF ISOBUTENE-CONTAINING FEEDSTOCKS

(75) Inventors: Stephen Harold Brown, Bernardsville, NJ (US); Georges Marie Mathys, Bierbeek (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 244 days.

(21) Appl. No.: 11/373,360

(22) Filed: Mar. 10, 2006

(65) Prior Publication Data

US 2007/0213576 A1      Sep. 13, 2007

(51) Int. Cl.
C07C 2/24 (2006.01)
C07C 45/00 (2006.01)
C07C 67/08 (2006.01)

(52) U.S. Cl. .................. 585/533; 585/510; 585/514; 585/520; 585/530; 585/532; 568/451; 568/452; 560/98

(58) Field of Classification Search .......... 585/520, 585/530–533, 326, 327, 329, 510, 514; 568/451, 568/452; 560/68
See application file for complete search history.

(56) References Cited

U.S. PATENT DOCUMENTS

| 3,657,150 A | 4/1972 | Juguin et al. ............... 252/435 |
| 4,962,249 A | 10/1990 | Chen et al. .................. 585/329 |
| 5,026,933 A | 6/1991 | Blain et al. ..................... 585/7 |
| 5,672,800 A | 9/1997 | Mathys et al. ............... 585/520 |
| 6,143,942 A | 11/2000 | Verrelst et al. ............... 585/533 |
| 6,969,736 B1 | 11/2005 | Godwin et al. ............... 524/296 |
| 2004/0006250 A1 | 1/2004 | Mathys et al. ................. 585/17 |
| 2004/0030212 A1 | 2/2004 | Al-Soufi et al. ............. 585/533 |
| 2004/0181106 A1 | 9/2004 | Nurminen et al. ........... 585/533 |
| 2005/0119508 A1 | 6/2005 | Clausi et al. ................. 568/451 |

FOREIGN PATENT DOCUMENTS

| EP | 0 625 132 | 11/1994 |
| EP | 0 703 888 | 4/1996 |
| EP | 0 757 976 | 2/1997 |
| EP | 1 167 326 | 1/2002 |
| WO | WO 93/16020 | 8/1993 |
| WO | WO 95/22516 | 8/1995 |
| WO | WO 01/83407 | 11/2001 |
| WO | WO 02/06191 | 1/2002 |
| WO | WO 02/060844 | 8/2002 |

OTHER PUBLICATIONS

"EMOGAS Technology for Catpoly Units", presented at the National Petrochemical & Refiners Association Annual Meeting, Mar. 13-15, 2005, San Francisco, CA, 18 pages.
Meunier et al., "High-Purity Isobutene Production by Decomposition of MTBE", vol. 46, 1991, France (French Translation), 43 pages.

*Primary Examiner*—In Suk Bullock
(74) *Attorney, Agent, or Firm*—Andrew B. Griffis

(57) ABSTRACT

The invention relates to the use of isobutene-containing olefin feedstock in oligomerization reactions, particularly in the production of octenes as feedstock for the manufacture of plasticizer alcohols, the process comprising contacting a feed comprising isobutene with a molecular sieve at a temperature in excess of 240° C. to produce a product low in triple-branched octenes.

18 Claims, 3 Drawing Sheets

Octenes Selectivity vs. Conversion

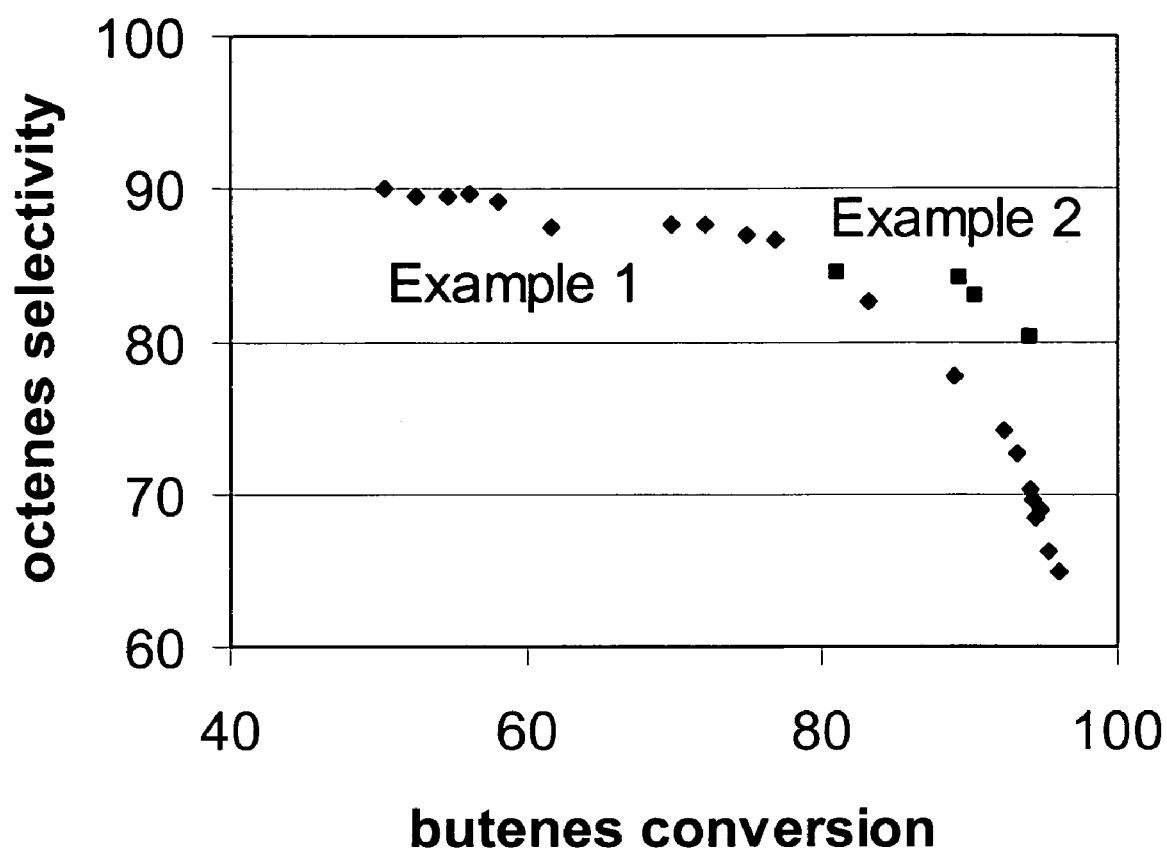
Figure 1 - Octenes Selectivity vs. Conversion

Figure 2 - Octenes Triple Branching vs. Conversion
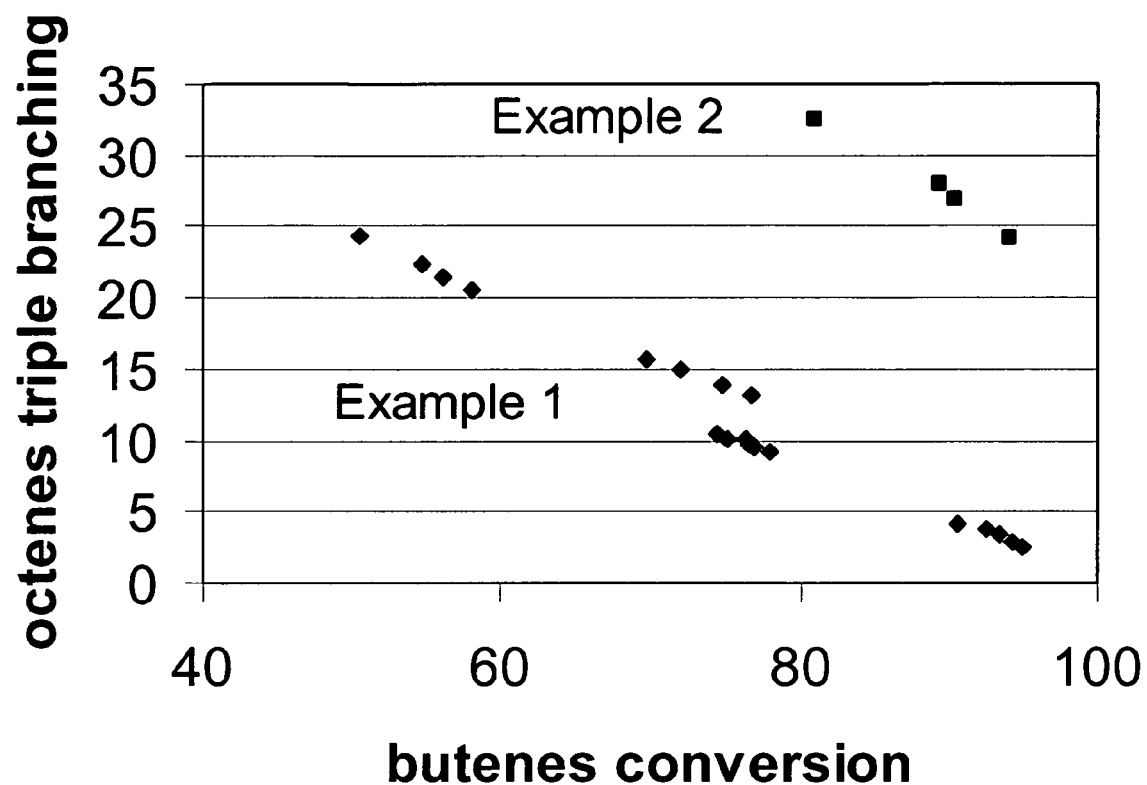

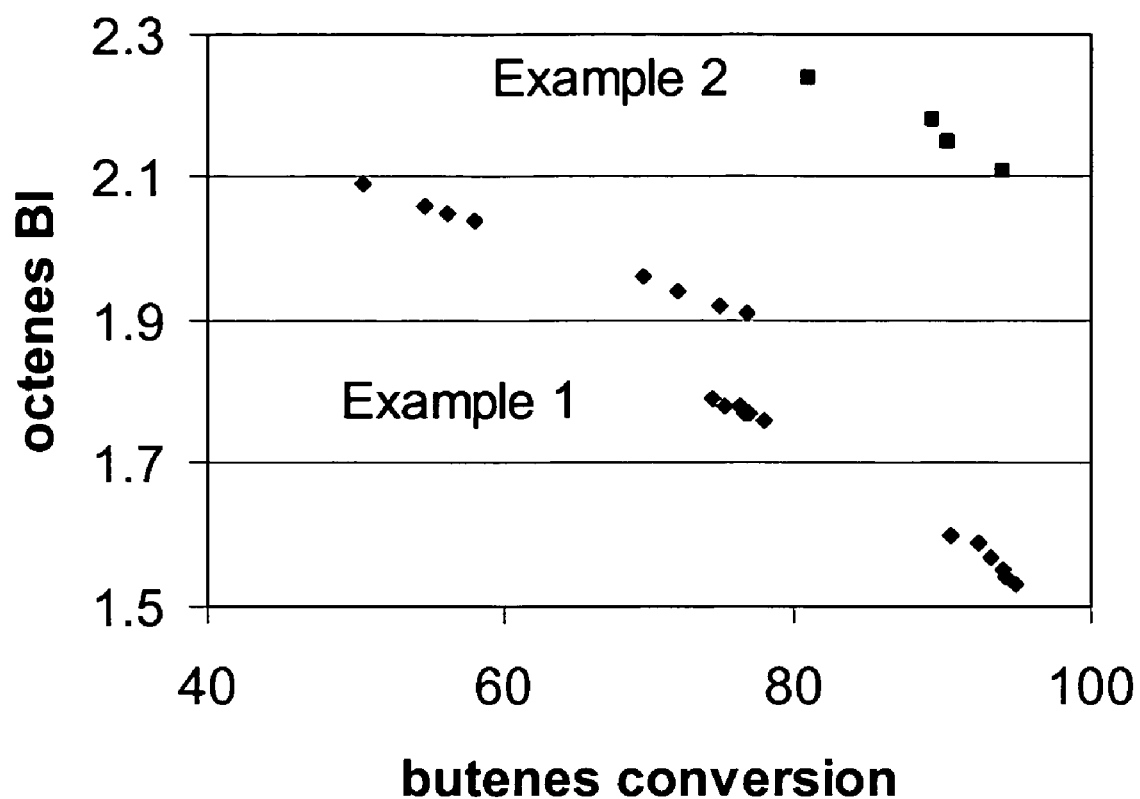
Figure 3 - Octenes Branch Index vs. Conversion

OLIGOMERIZATION OF ISOBUTENE-CONTAINING FEEDSTOCKS

FIELD OF THE INVENTION

The invention relates to the use of isobutene-containing olefin feedstock in oligomerization reactions, and in preferred embodiments the use of raffinate in the production of octenes as feedstock for the manufacture of plasticizer alcohols.

BACKGROUND OF THE INVENTION

The oligomerization of light olefins to heavier olefins is important for the production of gasoline, distillate, and feedstock for other processes. In these oligomerization processes typically C3 to C6 olefins and mixtures thereof are contacted with zeolite or solid phosphoric acid (SPA) catalyst under oligomerization conditions and converted to dimers, trimers, and other oligomers (low molecular weight polymers). The products may be useful "as is", or they may be further processed, such as by hydrogenation or to produce functionalized products.

By way of example, a typical direct product of dimerization of C4 olefins is trimethyl pentene, useful as an octane enhancer. See, for instance, U.S. 2004/0181106 and U.S. 2004/0030212. In this regard, the presence of isobutene in the feed enhances the production of the desired highly branched product.

Isobutene in light olefin oligomerization to gasoline in Catpoly units is also useful for improved octane values. Recent work to displace solid phosphoric acid with zeolites has shown that typically zeolites are excellent catalysts for producing highly branched, high octane oligomers from isobutene containing feeds. See "EMOGAS Technology for Catpoly Units", presented at the National Petrochemical & Refiners Association Annual Meeting, Mar. 13-15, 2005, San Francisco, Calif.; and U.S. Application No. 2004/0181106 A1.

The octenes produced by the aforementioned dimerization may instead be reacted with carbon monoxide and hydrogen in the well-known Oxo Process, to produce C9 aldehydes and/or alcohols. See, for instance, U.S. Patent Application No. 2005/0119508.

C9 aldehydes and/or alcohols have many uses and are particularly highly valued in the production of plasticizers, e.g., triisononyl phthalate. See, for instance, U.S. Pat. Nos. 3,657,150 and 6,969,736. The presence of isobutene has, in the past, presented problems in the production of plasticizers. As a result, the prior art concerning the use of zeolites to produce higher olefins for plasticizer production has in some cases focused on the presence of isobutene in the feedstock.

U.S. Patent Application Publication 2004/0006250 (WO 01-83407A1) teaches that the feedstock may comprise butenes obtained from refining or cracking and may comprise mixtures of n-butenes and isobutene having from a few wt % of isobutene up to 30 to 40 wt % isobutene at 140 to 240° C. A particular example discloses a mixed n-butene and isobutene feed to H-ZSM-57 with conditions adjusted to maintain total alkene conversion above 95%. In one example a feed comprising about 8 wt % isobutene gave a product comprising about 6.5 wt % trimethypentene with about 80 wt % octene selectivity.

C4 linear olefins are an attractive feedstock for producing octenes with zeolite catalysts because, among other reasons, the resulting octenes have triple branching of less than about 5 wt %. When isobutene is added to the oligomerization feedstock, the amount of triple-branched octenes increases to a level which is unacceptable for some end uses such as certain plasticizers.

The amount of isobutene in C4 streams typically obtained from the refinery operations (i.e., raffinate-1, or "raff-1") is greater than the amount used in current commercial oligomerization reactions leading to Oxo Process feedstock. Thus, isobutene is removed, yielding a product, "raff-2", useful in the Oxo Process for plasticizer-grade C9 alcohols. The isobutene removed in this step could be used in the production of, for instance, MTBE. However, with the phase out of MTBE, the usual integrated commercial process—where raff-1 was converted to raff-2 and simultaneously supplying the feed to Oxo and MTBE processes—is no longer practical.

Accordingly, for these reasons, it would be highly desirable if a process could be found to dimerize raff-1 directly, without a step of removal of all or a portion of isobutene, to yield a C8 product directly useful in the Oxo Process without removal of isobutene.

There is an extensive prior art teaching the use of zeolites for light olefin oligomerization, particularly for uni-dimensional 10-ring zeolites such as ZSM-22, ZSM-23, and SAPO-11. See, for instance, U.S. Pat. Nos. 4,962,249; 5,026,933; EP 0703888; EP 0625132; and EP 0757976. The present inventors have surprisingly discovered a process wherein multidimensional zeolites can, in embodiments, be used to oligomerize high isobutene-containing feedstocks, such as raffinate-1, to provide a product low in triple branched octenes.

SUMMARY OF THE INVENTION

The invention is directed to the oligomerization of isobutene-containing feedstocks over molecular sieves, preferably zeolites, and more preferably zeolites having the MFS structure type, to produce a product low in triple-branched octene isomers. In embodiments the catalysts comprise multi-dimensional molecular sieves containing at least one 10 or 12 ring channel system, e.g., ZSM-57.

The invention is also directed to a process for making functionalized C9 products (e.g., alcohols) comprising oligomerization of isobutene-containing raffinate-1 followed by reaction of at least a portion of the oligomerization product in the Oxo Process.

It is an object of the invention to provide an improved process for the oligomerization of isobutene, especially raffinate-1, wherein the improvement comprises producing a product having a decreased amount of branched octenes that is advantageously used in the Oxo Process to provide plasticizer-grade C9 alcohols.

It is still another object of the invention to provide, in embodiments, a process of oligomerizing high isobutene-content olefin feeds to provide selectively an octene product having less than 10 wt % triple-branched octene product with a branching index (BI) of less than 1.9, at temperatures in excess of 240 C. (reactor inlet temperature) and butene conversion rates of between about 80 and 95%.

These and other objects, features, and advantages will become apparent as reference is made to the following detailed description, preferred embodiments, examples, and appended claims.

BRIEF DESCRIPTION OF THE DRAWINGS

FIG. 1 is a graph showing the octene selectivity versus butene conversion using a ZSM-57 catalyst.

FIG. 2 is a graph showing octene triple branching versus butene conversion using a ZSM-57 catalyst.

FIG. 3 is a graph showing octene branchiness (BI) versus butene conversion using a ZSM-57 catalyst.

DETAILED DESCRIPTION

According to the invention, isobutene-containing feedstocks are oligomerized over molecular sieve catalysts effective for the oligomerization of C3 to C6 olefins to dimers and higher order oligomers, particularly over zeolites and even more preferably over zeolites having the MFS structure, as defined by the IZA structure commission and published in "Atlas of Zeolite Structure Types" by W. M. Meier et al., 4th revised Ed. Elsevier, London 1996. ZSM-57 is the preferred zeolite.

The preferred catalyst is ZSM-57, at least partially if not wholly in acidic form.

By "isobutene" is meant 2-methyl propene (or isobutylene).

The feedstock may more broadly be selected from and/or comprise a mixture of isobutene with one or more other C3-C6 linear and/or branched olefins (alkenes). In preferred embodiments the feedstock may comprise raffinate-1 or raff-1, the terms used interchangeably herein.

The preferred feedstock is raffinate-1, which is used interchangeably herein with "raff-1".

By "raff-1" is meant a C4 feedstock comprising >40% olefins and <1 wt % dienes obtained from FCC or thermal cracking units (e.g. cokers, visbreakers, and steancrackers) or combinations thereof. Raff-1 is typically obtained from a feedstock containing a broader range of hydrocarbons, typically C3 through C5. The mixed carbon number feed is sent through a depropanizer to remove C3 hydrocarbons and then through a debutanizer to remove C5+ hydrocarbons. The mixed C4 feedstock obtained in this fashion from steamcrackers contains 10 to 40 wt % butadiene. To obtain a raff-1 stream, the mixed steamcracker C4's are mixed with hydrogen and passed over a catalyst which selectively converts butadiene to linear butenes to provide a mixture of isobutene, n-butenes, isobutane, and n-butane with <1 wt % butadiene.

In addition to isobutene, the feedstock may contain a single other alkene or multiple other alkenes, mixtures of linear and branched alkenes with the same carbon number or mixtures of linear and/or branched alkenes with different carbon numbers. For example, suitable feedstreams include mixed $C_3$ and $C_4$ olefinic feeds obtained from refining, cracking (catalytic cracking or steam cracking) and/or reforming of oils, butane-butene fractions obtained by removing or selectively hydrogenating butadiene from $C_4$ by-product fractions formed in the production of ethylene by thermal cracking of oils (such fractions contain mixtures of n-butenes and isobutene having from a few wt % of isobutene up to 30 to 40 wt % isobutene) or $C_4$ hydrocarbon mixtures obtained by dehydrogenation of hydrocarbon mixtures containing n-butane and isobutane.

A particular embodiment of the invention relates to processes using a feedstock in which isobutene represents about 8 to about 40 wt %, such as from about 8 or 9 or 10 or 11 or 12 or 13 or 14 wt % to about 20 or 25 or 30 or 34 or 36 or 38 or 40 wt % isobutene, with ranges from any lower limit to any higher limit being envisioned, such as from 12 to 34 wt %, or from 8 to 20 wt %, or 12 to 20 wt %. Unless otherwise specified, through the specification when wt % of an olefin is referred to, it is based on the weight of all the olefins in the feedstock, whether mono-olefins or otherwise (such as butadiene); i.e., the paraffin content is ignored. Thus, for example, a feedstock comprised of 12 wt % isobutene, 48 wt % n-butenes, and 40 wt % butanes is computed to have an isobutene content of 20 wt %.

The feedstock may also comprise an inert diluent. The diluent is typically comprised of C2-C6 paraffins.

In preferred embodiment, the feedstock consists essentially of a mixture of isobutene (such as in any of the amounts specified above), one or more other C3-C6 linear and/or branched olefins (such as in the amount of 1 wt % to about less than 50 wt %), remainder paraffin diluent. In the most preferred embodiment, the feedstock consists essentially of a raff-1

In embodiments, using isobutene containing feedstocks, the process gives an oligomeric product low in triple-branched isomers, i.e., that contains from 2 to 15 wt % trimethylpentenes, preferably from 2 to 10 wt % trimethylpentenes, or 2 to 8 wt % trimethylpentenes, with respect to the total weight of octenes in the oligomeric product.

The average branchiness of the octenes produced by the process of the invention may be low, such as below 1.8 or 1.7, or even 1.6, but typically will range from 1.6 to 2.2, such as from about 1.6 to 2.2, or 1.7 to 2.0 or 1.7 to 1.9. Branchiness is defined as the number of branches per molecule or moiety (e.g., octene), and Branching Index (BI) is given here as the average number across the sample. Thus trimethylpentene has a branchiness of 3.0. A mixture of 50 mol % trimethylpentene and 50 mol % dimethylhexene has a BI of 2.5.

The catalyst may be chosen from among a variety of zeolites active for alkene oligomerization reactions (i.e., a catalyst other than solid phosphoric acid (SPA)). The preferred catalysts are multidimensional 10 and 12 ring zeolites such as zeolites having the MFS (e.g., ZSM-57), MFI (e.g., ZSM-5), MWW (MCM-22 family), MEL (e.g., ZSM-11), MTW (e.g., ZSM-12), or EUO (e.g., EU-1) structure type, or any member of the ferrierite, faujasite, mordenite, or structure zeolite L or zeolite Beta. It is one of the surprisingly discoveries of the present invention that in embodiments multidimensional zeolites can produce octenes with <10% triple branching and <1.9 branch index from high isobutene-containing feedstocks such as raffinate-1 by proper choice of reaction conditions. The term uni-dimensional means that the pore systems do not interact, i.e., there is a single pore throughout the zeolite, in contast to multidimensional systems, wherein the pore systems intersect, The one or more catalysts may be fully protonated, i.e. substantially all acid sites are in proton form or they may be partially protonated. A mixture of fully protonated and partially protonated catalysts may be used.

Without wishing to be bound by theory, the catalysts of the invention produce double and triple-branched octenes from isobutene containing feedstocks as the kinetic products (products at low feedstock olefin conversions). The kinetic products are converted by secondary isomerization reactions into the desirable lower-branched isomers. By finding reaction conditions at which secondary isomerization proceeds at similar rates to oligomerization, catalysts that produce triple-branched isomers as the dominant product at lower conversion can surprisingly produce, in preferred embodiments, a product with <10 wt % triple branched octene isomers at between 80 and 95% olefin conversion.

Octene product quality is a surprisingly strong function of temperature and feedstock olefin conversion. By operating at high single pass feedstock conversion (preferably 80-95 wt %; unless otherwise specified this means a weighted average of the individual conversions of all the olefin isomers in the feedstock) and a cycle-average reaction temperature of between 220 and 320° C. (such as between 230 and 310° C., in excess of 240 and 300° C. or in excess of 240 and 290° C.; also contemplated as preferred embodiments are any of the aforementioned lower ranges to any of the aforementioned upper ranges, such as 230 to 300 or 290 C., in excess of 240 to 320 or 310° C., and so on), a practical means is provided to use "non-selective" multi-dimensional 10 and 12 ring zeolite catalysts to produce higher olefin products suitable for the production of plasticizer alcohols. At least some of the objectives of the invention, such as in preferred embodiments triple branching of <10 wt % and BI of <1.9, are achieved within the preferred olefin (butenes) conversion of 80-95%.

It will be appreciated by one of skill in the art in possession of the present disclosure that at the start of cycle where temperature is lower, excellent product quality can none-the-less be achieved by operating at a higher conversion. At high conversions, secondary olefin disproportionation and oligomerization reactions become more important. Selectivity to octenes using a raff-1 feedstock can decline dramatically. This provides an economic incentive to operate at lower olefin conversion. While the directional response of product selectivity to conversion is not particularly surprising, the response to temperature is highly surprising. Increasing reaction temperature for raff-1 feedstock conversion improved catalyst activity, selectivity, and stability. The prior art, in contrast, emphasizes the need to find high activity catalysts which can operate a low temperature where improved selectivity is typically believed to occur. Thus, contrary to what was known, the most preferred solution according to the present invention is a less active multi-dimensional zeolite catalyst operating at a relatively high temperature for olefin oligomerization.

In preferred embodiments the catalyst contains a zeolite of the MFS structure type, such as ZSM-57 as disclosed in, for instance, EP-B-174121, U.S. Pat. Nos. 4,873,067 and 4,973,781.

Zeolite catalysts having crystal structures that are essentially the same as the MFS crystal structure but differing slightly therefrom in chemical composition may also be used, such as, zeolite catalysts obtained by removal of a number of aluminum atoms from, or by steaming of the zeolite, or zeolite catalyst obtained by addition of different elements, for example, by impregnation or cation exchange or by incorporation during the zeolite synthesis.

ZSM-57 crystals may be prepared by any suitable method, for example, by heating a reaction mixture containing a source of silicon oxide and a source of aluminium oxide. The crystals are then generally calcined in air or oxygen at a temperature exceeding 500° C., for example, at a temperature of 510 or 550° C. for, for example, 10 to 20 hours. The calcined material is preferably exchanged with ammonium ions ($NH_4^+$) and subjected to conditions under which the ammonium ions decompose, with the formation of ammonia and a proton, thus producing the acid form of ZSM-57. The zeolite may be fully protonated, i.e. substantially all acid sites are in proton form. Alternatively, the zeolite may be partially protonated. The acid form may also be obtained by acid exchange with, for example, hydrochloric acid.

Catalysts suitable for the present invention are commercially available and/or made by procedures known in the art. For instance, ZSM-57, ZSM-12, and MCM-22 family catalysts are commercially available from ExxonMobil Chemical Company. FAU, beta, ZSM-5, and mordenite are commercially available from PQ, Engelhard, and SudChemie.

A modified ZSM-57 may also be used. The term "modified" means ZSM-57 formed by a method in which an organic substance (organic promoter or template) is used to promote formation of aluminosilicate crystals (zeolite precursor crystals) having the desired MFS structure type. The uncalcined zeolite precursor crystals are exchanged with ammonium ions or protons, and the crystals are then calcined under conditions such that a portion of the organic promoter or of a decomposition product derived therefrom remains within the pores of the crystal.

Reference is made to the following documents disclosing the preparation of ZSM-57 or modified ZSM-57-containing catalyst: U.S. Pat. Nos. 4,873,067, 4,973,781, EP-B1-174, 121, EP-A-625132 as well as Ernst and Weitkamp in "Zeolite ZSM-57: Synthesis, Characterization and Shape Selective Properties", in "Catalysis and Adsorption Zeolites", Ed. G. Öhlmann et al., Elsevier Science Publishers, B. V. Amsterdam.

While it is preferred that the catalyst comprises solely ZSM-57, in embodiments the zeolite crystals may contain a minor proportion of another crystalline material, such as another zeolite structure type or quartz.

The zeolite may be used in the form of powders (including powders consisting wholly or in part of single crystals), or the zeolite crystals may instead be incorporated in shaped agglomerates, for example, tablets, extrudates or spheres, which may be obtained by combining the zeolite with a binder material that is substantially inert under the conditions employed in the oligomerization process.

The zeolite catalyst may be present in amount of from 1 to 99% by weight, based on the combined weight of the zeolite and binder material. As binder material, any suitable material may be used, for example, silica, metal oxides, or clays, such as montmorillonite, bentonite and kaolin clays, the clays optionally being calcined or modified chemically prior to use. Further examples of suitable matrix materials include silica-alumina, silica-berylia, silica-magnesia, silica-thoria, silica-titania, silica-alumina-magnesia, silica-alumina-thoria, silica-alumina-zirconia and silica-magnesia-zirconia.

In preferred embodiments using zeolites of the MFS structure type, the zeolite crystals may also be bound with another zeolite as disclosed for example in U.S. Pat. Nos. 5,993,642, 6,039,864, EP-B-568,566, EP-B-793,634 and EP-B-808, 298, all incorporated herewith by way of reference.

The alkene-containing feedstock comprising isobutene, is contacted with the molecular sieve catalyst, preferably a zeolite of the MFS structure type, or catalysts having crystal structures that are essentially the same as the MFS crystal structure, or modified MFS structure, as defined above, under oligomerization conditions effective to produce a product comprising octenes.

It should be noted that in practice carbonaceous deposits accumulate in the pores of zeolite catalysts when contacted with alkene-containing feedstocks. The deposits reduce the activity of the catalyst. To compensate for lost activity, the process of the invention increases the reaction temperature with time on stream. The triple branchiness and branch index of the products produced decrease with increasing reaction temperature. The process of the invention preferably produces a product with <10 wt % triple branched octenes and a total branch index of <1.9 at the average reactor temperature across the full temperature range of the cycle. In preferred embodiments, the conditions include a start of cycle temperature of from about 200° C., to about 250° C., such as about 220° C., 230° C. or in excess of 240° C. (as measured by reactor inlet temperature), and an end of cycle temperature of from about 280 to 350° C., such as about 290° C. or 310° C. Preferred full cycle temperature ranges are from any temperature within the start of cycle temperature range, such as 220° C., to any temperature within the end of cycle temperature range, such as to 300° C. Thus, at least during part of the cycle, reactor inlet temperatures will be about 250, 260, 270, 280° C., etc.

The pressure is preferably in the range of from 5 to 10 MPa, more preferably, from 6 to 8 MPa and at an alkene weight hourly space velocity (WHSV) preferably in the range of from 0.1 to 40, more preferably from 1 to 20, and most preferably from 3 to 12 weight/weight·hour.

A desired conversion level is generally obtained by first selecting a reaction temperature and by regularly adjusting this reaction temperature to compensate for catalyst deactivation over time. The process of the invention is highly selective at conversion rates as high as 95 wt %, typically comprised between 65 and 95 wt %, preferably comprised between 80 and 95 wt %. These conversion rates may be achieved without recycle, i.e., they are single-pass conversion rates.

The process of the invention provides a product containing an oligomeric product low in triple-branched octenes, and enriched in mono-branched octenes, which can be further transformed by any one or more of the following steps: fractionation, hydrogenation, hydroformylation, oxidation, carbonylation, etherification, epoxidation, hydration, and the like. Accordingly, the present invention also concerns higher aldehydes obtained by hydroformylation (such as by the Oxo Process), higher alcohols obtained by hydrogenation of the aforementioned higher aldehydes, and higher carboxylic acids obtained by oxidizing the aforementioned aldehydes or alcohols. (The term "higher" here simply means that the product has been oligomerized, e.g., dimerized, and then increased by one more carbon in the chain by the reaction with CO and $H_2$ in the well-known Oxo or hydroformylation reaction). The process of the invention also encompasses a process for the preparation of an ester of a polycarboxylic acid in which the higher alcohols derived from the oligomeric product are reacted with a polycarboxylic acid under conditions suitable to make the polycarboxylic esters. Preferred esters are phthalic or adipic esters.

A particular advantage of the present invention is that raffinate-1 from a refinery or petrochemical process may be used as the feedstock without removal of any or all of the isobutene present in the raffinate-1.

Raff-1 obtained from an FCC unit and or mixed FCC and coker and visbreaking units is typically enriched in paraffins (isobutane and butane). The higher paraffin content reduces the value of this type of raff-1 stream vs. raff-1 obtained from steamcracking. Unlike raff-1 from a steamcracker, raff-1 can be produced without selective diene hydrogenation from an FCC unit. The process of the invention enables production of plasticizers from FCC C4 olefins with minimal capital cost. Raff-1 is distilled from the FCC unit, the contained C4 olefins are converted to isononyl alcohols in high yield, and all the byproducts can be returned to the refinery for fuels blending.

Another particular advantage of the present invention is that the product of the oligomerization of raffinate-1 feedstock, as set forth above, may directly and, in preferred embodiments, without further purification, be contacted with a catalyst effective for the oxonation reaction, i.e., the transition metal catalyzed hydroformylation reaction, in the presence of CO and $H_2$ to provide a product comprising predominantly aldehydes containing one more carbon atom than the reacted olefin, and optionally then further reacted by hydrogenation, if necessary, to yield a C9 alcohol or reacted further by oxidation to yield a C9 carboxylic acid. In a particularly preferred embodiment, the C9 alcohols thus produced are converted to plasticizer by reaction with phthalic anyhydride, trimellitic anhydrides, adipic acid, and the like, to yield the corresponding tri- and/or di-substituted esters, which are particularly useful plasticizers in PVC and other resins. The products may also be advantageously employed as detergent intermediates, e.g., nonyl phenol.

The present invention has been described generally above, with reference to certain embodiments. The following specific examples are provided as "representative" and, although they may describe preferred embodiments, are not intended to limit the invention.

Materials: (a) 50% ZSM-57/50% alumina catalyst purchased commercially from ExxonMobil Chemical Company, was provided in the form of extrudate in its activated hydrogen form, is crushed and sized to 0.3 to 1.0 mm particles but otherwise used "as is". Pure feedstock components—n-butenes, isobutene and butanes are purchased from Air Liquide and used as received. Butene oligomerization is carried out with a 60 wt % butenes/40 wt % paraffin synthetic feedstock.

All experiments were conducted on standard pilot micro units with conditions chosen to closely emulate those used in commercial operations, e.g.: 130-300° C. and 70 bar (7,000 kPa). The feedstock is pumped from 50 liter vessels using displacement pumps controlled by mass flow meters. The feed is saturated with water by passing upwards through a vessel containing water at a constant 40° C. temperature. After exiting the hydrator the feed is pre-heated to the preselected heater temperature and then runs downwards through a fixed-bed reactor equipped with an internal thermowell. The oligomerization reaction is exothermic leading to a non-isothermal temperature profile down the length of the catalyst bed.

No C2 or C1 gasses are fed or produced, and there is no evidence of any feedstock cracking. The product is cooled to near room temperature and depressured to 20 bar. Total reactor effluent samples are taken at 20 bar. After flowing through the sample vessels, the effluent is depressured from 20 bar to atmospheric. Unreacted feedstock olefins and paraffins escape out the vent.

The total reactor effluent is analyzed by GC. The feed and product olefin/paraffin ratios are compared in order to measure conversion. Liquid product is analyzed on a standard commercial gas chromatograph (GC) equipped with a platinum catalyst to hydrogenate product olefins to paraffins. Carbon number distribution and paraffin distribution is determined. Conversion (%)=$[1-\{(A_{olefin}/A_{paraffins})/(A^{\circ}_{olefin}/A^{\circ}_{paraffins})\}]\times 100$, where A=chromatographic peak area in product analysis (wt %) and $A^{\circ}$=chromatographic peak area in feed analysis (wt %). Selectivity is determined from gas chromatographic peak areas, after hydrogenation of the reaction product stream according to the following equation: $S_{Cn}=A_{Cn}/\Sigma_i A_{Ci}$, where $A_{Cn}$=chromatographic peak area of all isomers with carbon number n, and $A_{Ci}$=chromatographic peak area of all isomers with carbon number other than n. The terms "conversion" and "selectivity" are more fully described in U.S. Patent Application No. 2004/0006250A1, and reference(s) cited therein The conversion and selectivity values referred to hereinafter, including the claims, are for butene conversion and octene selectivity, unless otherwise stated.

EXAMPLE 1

Commercial ZSM-57/alumina extrudates were used to process 12 wt % isobutene/48 wt % n-butene/10 wt % isobutane/30 wt % n-butane feedstock. Reaction conditions were 70 bar, 15 WHSV, and 235° C. or 275° C. feedstock inlet temperature. Octenes selectivity vs. conversion is plotted using diamonds in FIG. 1. A single continuous curve is obtained indicating that octenes selectivity is nearly independent of reaction temperature. Product triple branching vs.

butanes conversion is plotted using diamonds in FIG. 2. The branch index data falls onto two separate groups. The group between 40 and 75% conversion forms a line at higher triple branching. The group between 70 and 95% conversion forms a line at lower triple branching. Product branch index (BI) vs. conversion is plotted using diamonds in FIG. 3. The group between 40 and 75% conversion forms a line at higher branch index. The group between 70 and 95% conversion forms a line at lower branch index. Triple branching and branch index are proven to be a function of temperature. Higher temperature operation leads to a desirable reduction in octenes triple branching and branch index.

EXAMPLE 2

Commercial ZSM-57/alumina extrudates were used to process 20 wt % isobutene/46 wt % n-butene/16 wt % isobutane/18 wt % n-butane feedstock. Reaction conditions were 70 bar, 15 WHSV, and 175° C. feedstock inlet temperature. Octenes selectivity vs. butanes conversion is plotted in FIG. 1. Percent triple branched isomers in the octenes (octene triple branching) vs. conversion is plotted in FIG. 2. Octenes branching index (BI) vs. conversion is plotted in FIG. 3. At 175° C. the product retains high levels of triple branched products and high BI even at 95% conversion.

High temperature and conversion operation leads to a step-change decrease in octenes triple branching. Above 90% conversion operating at high temperature reduces the octenes triple branching content from 25 wt % in example 2 to below 5 wt % in Example 1 (FIG. 2). Between 75 and 85% conversion there is surprisingly no octenes selectivity penalty for the high temperature operation. Octenes triple branching decreases with increasing conversion (FIG. 2).

The results show that even with isobutene/total butenes ratio greater than 0.10, an octene product is obtained with less than 10 wt % triple branched product by operating at a sufficiently higher temperature. This is surprising, as well as contrary to the prior art, which teaches a triple branched content of greater than 10 wt % at an isobutene/total butenes ratio greater than 0.10. Without wishing to be bound by theory, the successful results suggest isomerization of double and triple branched octenes to mono-branched octenes at much faster rates than oligomerization to trimers and tetramers accompanied by disproportionation. The preferred catalyst, ZSM-57, does a remarkably good job of suppressing further oligomerization of octenes, while facilitating unimolecular isomerization. Prior to the present invention it was believed that zeolites ZSM-22 and ZSM-23 were uniquely active for secondary isomerization of octenes.

Trade names used herein are indicated by a ™ symbol or ® symbol, indicating that the names may be protected by certain trademark rights, e.g., they may be registered trademarks in various jurisdictions.

All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains. Among those features, the preferred embodiment include: a process comprising contacting an isobutene-containing feed with a multi-dimensional molecular sieve catalyst containing at least one 10 or 12 ring channel system under oligomerization conditions effective to produce a product comprising octenes comprising less than about 10 wt % triple-branched octenes, based on the weight of said octenes, and having an octenes branch index of <2, preferably wherein said conditions are characterized by a temperature, measured at the reactor inlet, from about 220° C. to about 320° C., or in excess of 240° C. to about 320° C.; or any of the aforementioned wherein said catalyst is selected from ZSM-57, ZSM-5, FAU, Beta, ZSM-12, mordenite, MCM-22 family, and mixtures thereof, particularly wherein said catalyst is selected from fully and/or partially protonated ZSM-57, or wherein said catalyst comprises at least 90 wt % fully and/or partially protonated ZSM-57; or any of the aforementioned wherein said feed comprises raffinate-1, which may be further characterized as including greater than 10 wt % isobutene, based on the weight of the olefins in said feed; or any of the aforementioned wherein said product comprising octenes comprising less than about 8 wt % triple-branched octenes, based on the weight of said octenes, or wherein said feed comprises from 12 to 40 wt % isobutene, based on the weight of the olefins in said feed, or wherein said feed comprises from 12 to 34 wt % isobutene, based on the weight of the olefins in said feed, or wherein said feed comprises from 8 to 20 wt % isobutene, based on the weight of the olefins in said feed; or any of the aforementioned wherein said product comprises less than 8 wt % triple-branched octene, or wherein said product comprises octenes having a branchiness of from 1.7 to 2.2, or 1.6 to 2.1 or 1.5 to 2.0 or 1.4 to 1.9, or any of the lower BI given to any of the upper BI given; or any of the aforementioned wherein said conditions are further characterized as effective for single pass butenes conversion of from 80% to about 95%, or wherein said conditions are further characterized as effective for single pass butenes conversion of about 80% to about 90%; or any of the aforementioned processes further comprising the step of contacting said product comprising octenes with carbon monoxide and $H_2$ in the presence of a hydroformylation catalyst under conditions effective to produce a C9 alcohol product, which may still be further be characterized as further comprising the step of contacting said C9 alcohol product with at least one acid or acid anhydride to produce an ester of said C9 alcohol and said at least one acid or acid anhydride (such as wherein said at least one acid or acid anhydride is selected from phthalic acid and/or anhydride, mellitic acid and/or trimellitic anhydride, adipic acid, and mixtures thereof) and yet still further characterized as comprising the step of mixing said ester with PVC to form a plasticized PVC and extruding said plasticized PVC to form a shaped article.

The invention has been described above with reference to numerous embodiments and specific examples. Many variations will suggest themselves to those skilled in this art in light of the above detailed description. All such obvious variations are within the full intended scope of the appended claims.

What is claimed is:

1. A process comprising contacting an isobutene-containing feed having a isobutene/total butene ratio of greater than 0.10, with a multi-dimensional molecular sieve catalyst containing at least one 10 or 12 ring channel system under oligomerization conditions effective to produce a product comprising octenes, said conditions including a temperature, measured at the reactor inlet, in excess of 240° C. to about 320° C., said octenes comprising less than 10 wt % triple-branched octenes, based on the weight of said octenes, and having an octenes branch index of <2.

2. The process of claim 1, wherein said catalyst is selected from ZSM-57, ZSM-5, FAU, Beta, ZSM-12, mordenite, MCM-22 family, and mixtures thereof.

3. The process of claim 2, wherein said catalyst is selected from fully and/or partially protonated ZSM-57.

4. The process of claim 1, wherein said catalyst comprises at least 90 wt % fully and/or partially protonated ZSM-57.

5. The process of claim 1, wherein said feed comprises raffinate-1.

6. The process of claim 1, wherein said product comprising octenes comprising less than about 8 wt % triple-branched octenes, based on the weight of said octenes.

7. The process of claim 1, wherein said feed comprises from 12 to 40 wt % isobutene, based on the weight of the olefins in said feed.

8. The process of claim 1, wherein said feed comprises from 12 to 30 wt % isobutene, based on the weight of the olefins in said feed.

9. The process of claim 1, wherein said feed comprises from 8 to 20 wt % isobutene, based on the weight of the olefins in said feed.

10. The process of claim 1, wherein said product comprises less than 8 wt % triple-branched octene.

11. The process of claim 1, wherein said product comprises octenes having octene branching index of less than 1.9.

12. The process of claim 1, wherein said conditions are further characterized as effective for single pass butenes conversion of from 80% to about 95%.

13. The process of claim 1, wherein said conditions are further characterized as effective for single pass butenes conversion of greater than 80% to about 95%.

14. The process of claim 1, wherein said conditions are further characterized as effective for single pass butenes conversion of about 80% to about 90%.

15. The process of claim 1, further comprising the step of contacting said product comprising octenes with carbon monoxide and $H_2$ in the presence of a hydroformylation catalyst under conditions effect to produce a C9 alcohol product.

16. The process of claim 15, further comprising the step of contacting said C9 alcohol product with at least one acid or acid anhydride to product an ester of said C9 alcohol and said at least one acid or acid anhydride.

17. The process of claim 16, wherein said at least one acid or acid anhydride is selected form phthalic acid and/or anhydride, mellitic acid and/or trimellitic anhydride, adipic acid, and mixtures thereof.

18. The process of claim 17, further comprising the step of mixing said ester with PVC to form a plasticized PVC and extruding said plasticized PVC to form a shaped article.

* * * * *